United States Patent
Suyama et al.

(10) Patent No.: US 10,660,511 B2
(45) Date of Patent: May 26, 2020

(54) IMAGE PICKUP MODULE AND ENDOSCOPE

(71) Applicant: OLYMPUS CORPORATION, Tokyo (JP)

(72) Inventors: Takuro Suyama, Ina (JP); Takatoshi Igarashi, Ina (JP); Kensuke Suga, Nagano (JP); Yoshiro Nishimura, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/416,522

(22) Filed: May 20, 2019

(65) Prior Publication Data

US 2019/0274529 A1    Sep. 12, 2019

Related U.S. Application Data

(63) Continuation of application No. PCT/JP2017/023587, filed on Jun. 27, 2017.

(30) Foreign Application Priority Data

Nov. 21, 2016 (WO) .................. PCT/JP2016/084497

(51) Int. Cl.
*A61B 1/04* (2006.01)
*A61B 1/05* (2006.01)
(Continued)

(52) U.S. Cl.
CPC .......... *A61B 1/051* (2013.01); *A61B 1/00009* (2013.01); *A61B 1/00114* (2013.01);
(Continued)

(58) Field of Classification Search
CPC .................................................... H04N 5/369
(Continued)

(56) References Cited

U.S. PATENT DOCUMENTS

2009/0166784 A1* 7/2009 Honda ................ H01L 31/0203
257/432
2009/0256229 A1* 10/2009 Ishikawa ................ H01L 24/97
257/434
(Continued)

FOREIGN PATENT DOCUMENTS

EP           2913850 A1     9/2015
JP        2005-334509 A    12/2005
(Continued)

OTHER PUBLICATIONS

International Search Report dated Aug. 1, 2017 issued in PCT/JP2017/023587.

*Primary Examiner* — Fabio S Lima
(74) *Attorney, Agent, or Firm* — Scully, Scott, Murphy & Presser, P.C.

(57) ABSTRACT

An image pickup module includes a plurality of semiconductor devices laminated via a sealing layer a signal is transmitted via a signal cable connected to a rear surface of the image pickup module, a first semiconductor device has a semiconductor circuit portion in a central area on a first principal plane, through wires in an intermediate area and first electrodes connected to the through wires in the central area on a second principal plane, the second semiconductor device has second electrodes in the central area on a third principal plane, and an external connection terminal to which the signal cable is connected, on a rear surface, and the sealing layer includes a first sealing layer arranged in the central area and a second sealing layer disposed in an outer circumferential area surrounding the intermediate area and with a Young's modulus smaller than a Young's modulus of the first sealing layer.

12 Claims, 11 Drawing Sheets

(51) Int. Cl.
| | |
|---|---|
| *H01L 23/00* | (2006.01) |
| *A61B 1/00* | (2006.01) |
| *A61B 1/045* | (2006.01) |
| *H01L 23/31* | (2006.01) |
| *H04N 5/225* | (2006.01) |
| *G02B 23/24* | (2006.01) |
| *H01L 27/146* | (2006.01) |
| *H01L 23/48* | (2006.01) |
| *H01L 23/538* | (2006.01) |
| *H04N 5/369* | (2011.01) |
| *H01L 21/768* | (2006.01) |

(52) U.S. Cl.
CPC .......... *A61B 1/00124* (2013.01); *A61B 1/045* (2013.01); *G02B 23/2484* (2013.01); *H01L 23/3142* (2013.01); *H01L 23/481* (2013.01); *H01L 23/5384* (2013.01); *H01L 23/562* (2013.01); *H01L 24/14* (2013.01); *H01L 24/16* (2013.01); *H01L 24/17* (2013.01); *H01L 27/1469* (2013.01); *H04N 5/22521* (2018.08); *H04N 5/369* (2013.01); *H01L 21/76898* (2013.01); *H01L 27/14618* (2013.01); *H01L 27/14634* (2013.01); *H01L 27/14636* (2013.01); *H01L 2224/02375* (2013.01); *H01L 2224/02377* (2013.01); *H01L 2224/02379* (2013.01); *H01L 2224/1403* (2013.01); *H01L 2224/14141* (2013.01); *H01L 2224/14177* (2013.01); *H01L 2224/16145* (2013.01); *H01L 2224/17517* (2013.01); *H01L 2924/00014* (2013.01); *H01L 2924/3512* (2013.01); *H04N 2005/2255* (2013.01)

(58) Field of Classification Search
USPC .......................................................... 348/45
See application file for complete search history.

(56) References Cited

U.S. PATENT DOCUMENTS

| | | | |
|---|---|---|---|
| 2014/0264698 A1* | 9/2014 | Huang | ............. H01L 27/14689 257/433 |
| 2015/0228678 A1 | 8/2015 | Yoshida et al. | |
| 2016/0365298 A1* | 12/2016 | Yamada | ................. H01L 23/13 |
| 2017/0164818 A1 | 6/2017 | Ishikawa et al. | |

FOREIGN PATENT DOCUMENTS

| | | |
|---|---|---|
| JP | 2010-273757 A | 12/2010 |
| JP | 2014-086546 A | 5/2014 |
| JP | 2014-094237 A | 5/2014 |
| JP | 5964003 B1 | 8/2016 |
| JP | 2016-201425 A | 12/2016 |
| WO | WO 2014/065099 A1 | 5/2014 |
| WO | WO 2016/111075 A1 | 7/2016 |
| WO | WO 2016/166890 A1 | 10/2016 |

* cited by examiner

IMAGE PICKUP MODULE AND ENDOSCOPE

CROSS REFERENCE TO RELATED APPLICATION

This application is a continuation application of PCT/JP2017/023587 filed on Jun. 27, 2017 and claims benefit of PCT/JP2016/084497 filed on Nov. 21, 2016, the entire contents of which are incorporated herein by this reference.

BACKGROUND OF THE INVENTION

1. Field of the Invention

The present invention relates to an image pickup module in which a plurality of semiconductor devices including an image pickup device are bonded, and an endoscope including the image pickup module in which the plurality of semiconductor devices including the image pickup device are bonded.

2. Description of the Related Art

An endoscope acquires an image of an inside of a body of a patient by inserting an insertion portion accommodating an image pickup module in a rigid distal end portion of the insertion portion, for example, into the body of the patient. Japanese Patent Application Laid-Open Publication No. 2005-334509 discloses an image pickup module in which a circuit board on which electronic part chips constituting a drive circuit, such as a capacitor, a resistance and an IC, are implemented is bonded to a back surface of an image pickup device.

A length of the image pickup module having the circuit board on which the electronic part chips are implemented in an optical axis direction is long. Therefore, it is not easy to shorten the rigid distal end portion of the endoscope.

Recently, a semiconductor device on which a planar device (a thin film part) having a same function as an electronic part chip such as a capacitor is formed has been developed. By bonding the semiconductor device on which the planar device is formed to a back surface of an image pickup device by a flip chip method, it is possible to thin and shorten an image pickup module.

By work for incorporation into a case or a bending operation of an endoscope, tensile stress is applied to a signal cable bonded to a rear surface of an image pickup module.

As disclosed in Japanese Patent Application Laid-Open Publication No. 2016-201425, an image pickup device is thin and, therefore, easily bends and deforms by stress.

For example, when cover glass is adhered via an adhesive layer to protect a light receiving portion, the image pickup device may bend and deform.

SUMMARY OF THE INVENTION

An image pickup module of an embodiment of the present invention is provided with: a plurality of semiconductor devices including image pickup devices; and sealing layers disposed between the plurality of semiconductor devices respectively; the image pickup module transmitting a signal via a signal cable connected to a rear surface; wherein a first semiconductor device among the plurality of semiconductor devices includes a first principal plane and a second principal plane facing the first principal plane and includes a semiconductor circuit portion in a central area on the first principal plane, first through wires connected to the semiconductor circuit portion existing in an intermediate area surrounding the central area, and first electrodes connected to the first through wires being disposed on the second principal plane; a second semiconductor device among the plurality of semiconductor devices includes a third principal plane and a fourth principal plane facing the third principal plane, second electrodes bonded to the first electrodes via bonding portions being disposed on the third principal plane, and second through wires connected to the second electrodes existing in the intermediate area; an external connection terminal is disposed on the rear surface of a semiconductor device on a rearmost side among the plurality of semiconductor devices, the signal cable being connected to the external connection terminal, and the external connection terminal being connected to the second through wires; and the sealing layers include a first sealing layer disposed in the central area and a second sealing layer disposed in an outer circumferential area surrounding the intermediate area and with a Young's modulus smaller than a Young's modulus of the first sealing layer.

An endoscope of another embodiment is provided with: an image pickup module, a signal cable, an insertion portion where the image pickup module is accommodated in a distal end portion, an operation portion disposed on a proximal end side of the insertion portion, and a universal cord extending from the operation portion, wherein the universal cord is electrically connected to the signal cable. The image pickup module is provided with: a plurality of semiconductor devices including image pickup devices, and sealing layers disposed between the plurality of semiconductor devices respectively, the image pickup module transmitting a signal via a signal cable connected to a rear surface. A first semiconductor device among the plurality of semiconductor devices includes a first principal plane and a second principal plane facing the first principal plane and includes a semiconductor circuit portion in a central area on the first principal plane, first through wires connected to the semiconductor circuit portion existing in an intermediate area surrounding the central area, and first electrodes connected to the first through wires being disposed on the second principal plane; a second semiconductor device among the plurality of semiconductor devices has a third principal plane and a fourth principal plane facing the third principal plane, second electrodes bonded to the first electrodes via bonding portions being disposed on the third principal plane, and second through wires connected to the second electrodes existing in the intermediate area; an external connection terminal is disposed on the rear surface of a semiconductor device on a rearmost side among the plurality of semiconductor devices, the signal cable being connected to the external connection terminal, and the external connection terminal being connected to the second through wires; and the sealing layers include a first sealing layer disposed in the central area and a second sealing layer disposed in an outer circumferential area surrounding the intermediate area and with a Young's modulus smaller than a Young's modulus of the first sealing layer.

DETAILED DESCRIPTION OF THE PREFERRED EMBODIMENT(S)

First Embodiment

An image pickup module 1 of the present embodiment (hereinafter referred to as "an image pickup module 1") is accommodated in a distal end portion 9A of an endoscope 9 (see FIG. 21).

Figure 1:
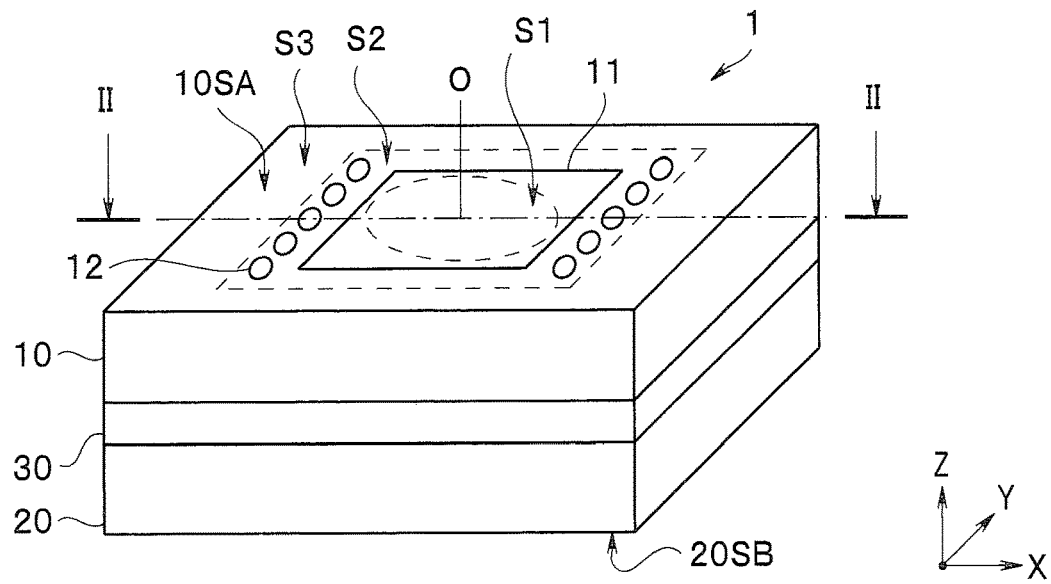
FIG. 1 is a perspective view of an image pickup module of a first embodiment.
Figure 2:
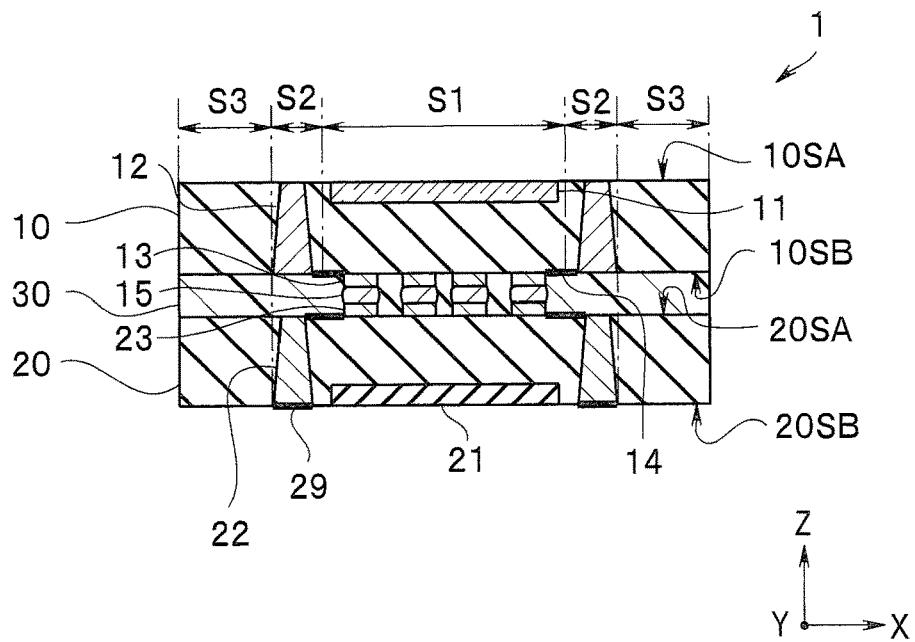
FIG. 2 is a cross-sectional view of the image pickup module of the first embodiment along a II-II line in FIG. 1.

As shown in FIGS. 1 and 2, in the image pickup module 1 of the present embodiment, an image pickup device 10, which is a first semiconductor device, and a second semiconductor device 20 are laminated via a sealing layer 30 disposed between the image pickup device 10 and the second semiconductor device 20. In other words, in the image pickup module 1, a plurality of semiconductor devices 10 and 20 including the image pickup device 10 are laminated.

Note that it should be noted that, in description below, drawings based on each embodiment are schematic, and a relationship between thickness and width of each portion, a thickness ratio, relative angles and the like among respective portions are different from actual ones; and, among the drawings, portions having a different mutual dimensional relationship or ratio may be included. The image pickup device 10 side and the second semiconductor device 20 side along an optical axis O (a Z axis) are referred to as "front" and "back", respectively.

Figure 11:
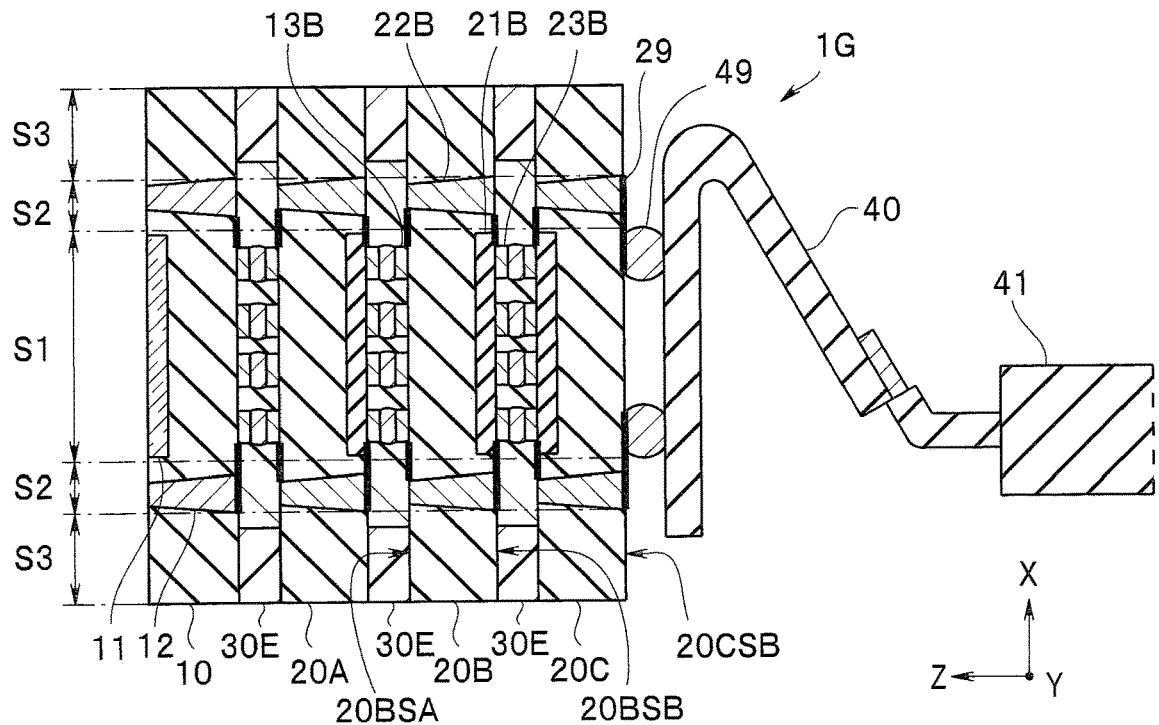
FIG. 11 is a cross-sectional view of an image pickup module of a third embodiment.

A part of components (for example, a circuit board 40 and a signal cable 41) may not be shown. That is, the circuit board 40 is connected to an external connection terminal 29 on a rear surface 20SB of the second semiconductor device 20 of the image pickup module 1, and, furthermore, the signal cable 41 is connected to the circuit board 40 as shown in FIG. 11 though it is not shown in FIG. 1 and the like.

That is, in the image pickup module 1, the plurality of semiconductor devices 10 and 20 including the image pickup device 10 are laminated via the sealing layer 30, and the image pickup module 1 transmits a signal via the signal cable 41 connected to the rear surface 20SB. The image pickup module 1 has the external connection terminal 29 disposed on the rear surface 20SB of the second semiconductor device 20 on a rearmost side between the plurality of semiconductor devices 10 and 20, the signal cable 41 being to be connected to the external connection terminal 29.

The image pickup device 10 in a rectangular shape in a plan view, that is, the image pickup device 10 the cross-sectional shape of which in a direction orthogonal to the optical axis O is rectangular is a substantially rectangular parallelepiped plate having a first principal plane 10SA and a second principal plane 10SB facing the first principal plane 10SA.

A light receiving portion 11, which is a first semiconductor circuit portion formed in a part of a central area S1 of the first principal plane 10SA, is a CCD or a CMOS light receiving circuit or the like and is configured to generate an electrical signal by receiving light and performing photoelectric conversion. The light receiving portion 11 is connected to a plurality of first electrodes 13 disposed in the central area S1 on the second principal plane 10SB via a plurality of through wires (first through wires) 12 disposed in an intermediate area S2 surrounding the central area S1.

In other words, the intermediate area S2 is an area where the plurality of through wires 12 are disposed; the central area S1 is an area inside the intermediate area S2; and an outer circumferential area S3 is an area surrounding the intermediate area S2. It is preferable that the central area S1 is included in an area facing the light receiving portion 11 (see FIG. 1).

Figure 3:
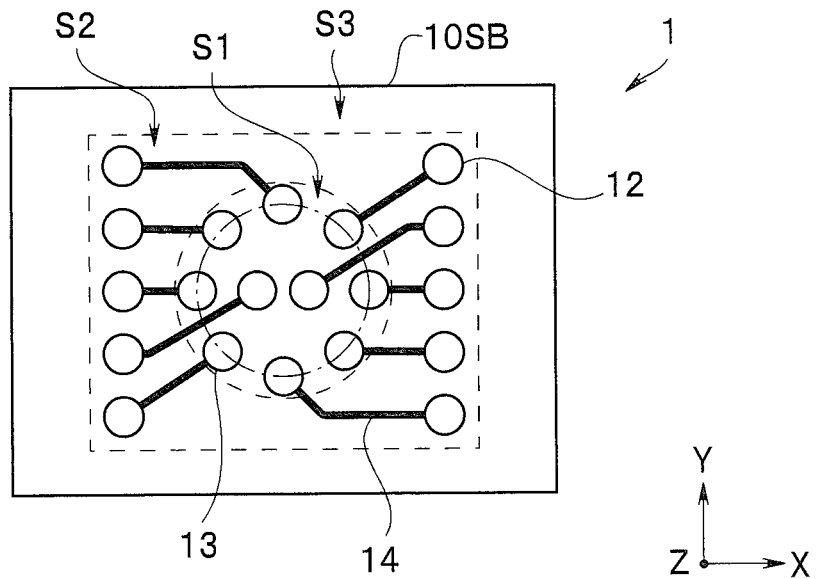
FIG. 3 is a rear view of an image pickup device of the image pickup module of the first embodiment.

As shown in FIG. 3, wires 14 connecting the through wires 12 in the intermediate area S2 and the first electrodes 13 in the central area S1 are disposed on the second principal plane 10SB of the image pickup device 10.

The second semiconductor device 20 in a rectangular shape in a plan view has a third principal plane 20SA and a fourth principal plane 20SB which is a rear surface facing the third principal plane 20SA. The second semiconductor device 20 has a plurality of second electrodes 23 bonded to the plurality of first electrodes 13 of the image pickup device 10, respectively, on the third principal plane 20SA. That is, the second electrodes 23 are disposed in the central area S1 on the third principal plane 20SA of the second semiconductor device 20.

The first electrodes 13 and the second electrodes 23 are bonded via bumps 15 with a height of 1 μm to 50 μm, which are bonding portions. Note that the first electrodes 13 and the second electrodes 23 may be bonded not via the bumps but directly.

The second semiconductor device 20 processes an electrical signal outputted by the image pickup device 10 and outputs the electrical signal as an image pickup signal. On the third principal plane 20SA or the fourth principal plane 20SB of the second semiconductor device 20, a planar device 21 which is a second semiconductor circuit portion constituting an electronic part function circuit such as a capacitor, a resistance, a buffer or the like or a signal processing circuit such as a noise removal circuit or an analog-digital conversion circuit. Note that FIG. 2 shows an example in which the planar device 21 is formed on the fourth principal plane 20SB.

The image pickup module 1 is a wafer level module fabricated by cutting a bonded wafer obtained by bonding an image pickup wafer including a plurality of image pickup devices 10 and a second semiconductor wafer including a plurality of the second semiconductor devices 20. Therefore, a projected image of the image pickup device 10 and a projected image of the second semiconductor device 20 that are projected on a projection plane in the direction orthogonal to the optical axis completely overlap with each other. Therefore, the image pickup module 1 is thin. Further, the image pickup module 1 in which the second semiconductor device 20 on which the planar device 21 is formed is bonded to the image pickup device 10 is short and small.

In the case of the wafer level module, it is possible to efficiently fabricate a plurality of image pickup modules 1. The image pickup module 1 may be a block level module obtained by cutting each wafer into rectangular or square blocks each of which includes a plurality of devices, bonding a plurality of blocks and then dividing into pieces. The block level module has a higher degree of freedom in arrangement of devices on a wafer than the wafer level module.

Note that through wires (second through wires) 22 connected to the second electrodes 23 of the second semiconductor device 20 exist in the intermediate area S2. The second electrodes 23 of the second semiconductor device 20 are connected to the planar device 21 on the fourth principal plane 20SB via the through wires (the second through wires) 22. That is, on the third principal plane 20SA of the second semiconductor device 20, wires connecting the second electrodes 23 in the central area S1 and the through wires 22 in the intermediate area S2 are disposed, though it is not shown.

The sealing layer 30 is disposed between the image pickup device 10 and the second semiconductor device 20. The sealing layer 30 is made of insulating resin such as epoxy resin, acrylic resin, polyimide resin, silicone resin or polyvinyl resin.

Each of thicknesses of the image pickup device 10 and the second semiconductor device 20 is about 5 μm to 100 μm, and the thicknesses may differ from each other as described later. The planar device 21 may be formed on only one side or both sides of the second semiconductor device 20.

In the image pickup module 1, the bonding portions between the first electrodes 13 of the image pickup device 10 and the second electrodes 23 of the second semiconductor device 20 are made of metal. Since an elastic deformation range of metal is small, when large stress is applied, cracks may occur on the bonding portion, or a bonding surface may be detached.

In the image pickup module 1, all the bonding portions are disposed in the central area S1, and the sealing layer 30 is disposed between the image pickup device 10 and the second semiconductor device 20. The sealing layer 30 made of resin has a large elastic deformation range and absorbs stress by elastically deforming.

That is, in the image pickup module 1, though the central area S1 has a so-called rigid structure, the outer circumferential area S3 surrounding the intermediate area S2 has a so-called flexible structure which is more flexible than the central area S1.

As already explained, the stress applied to the image pickup module 1 is applied via a signal cable (not shown) bonded to the second semiconductor device 20 which is the rear end surface of the image pickup module 1.

Here, force is applied to the image pickup module 1 via the signal cable by a bending operation of the endoscope. More specifically, force in such a direction that presses and bends the optical axis O is applied to the image pickup module 1 in which the semiconductor devices are laminated in a Z direction. Therefore, a position at which the stress is applied most is an outer side of the image pickup module 1, that is, the outer circumferential area S3.

Since all the bonding portions are disposed only in the central area S1 away from the outer circumferential area S3, reliability of the image pickup module 1 is high. Furthermore, in the image pickup module 1, since the sealing layer 30 disposed in the outer circumferential area S3 absorbs stress by elastically deforming, stress applied to the bonding portions (the bumps 15) and the through wires 12 and 22 is reduced.

In an image pickup module for endoscope of the present invention, a plurality of semiconductor devices including an image pickup device are laminated via a sealing layer to transmit a signal via a signal cable connected to a rear surface; a first semiconductor device among the plurality of semiconductor devices has a first principal plane and a second principal plane facing the first principal plane, has a semiconductor circuit portion in a central area on the first principal plane, has through wires connected to the semiconductor circuit portion in an intermediate area surrounding the central area and has first electrodes connected to the through wires in the central area on the second principal plane; a second semiconductor device among the plurality of semiconductor devices has a third principal plane and a fourth principal plane facing the third principal plane, has second electrodes in the central area on the third principal plane and has an external connection terminal to which the signal cable is to be connected, the external connection terminal being disposed on a rear surface of a semiconductor device on a rearmost side between the plurality of semiconductor devices; and bonding portions between the first electrodes and the second electrodes are disposed only in the central area.

Modifications of First Embodiment

Since an image pickup module of a modification of the first embodiment is similar to the image pickup module 1 and has same effects, a component with a same function will be given a same reference numeral, and description of the component will be omitted.

Modification 1 of First Embodiment

In the image pickup module 1, the plurality of first electrodes 13 and the plurality of second electrodes 23 disposed in the central area S1 are arranged in a circle. In other words, the bumps 15 which are bonding portions between the first electrodes 13 and the second electrodes 23 are arranged on a circumference of one circle.

Figure 4:
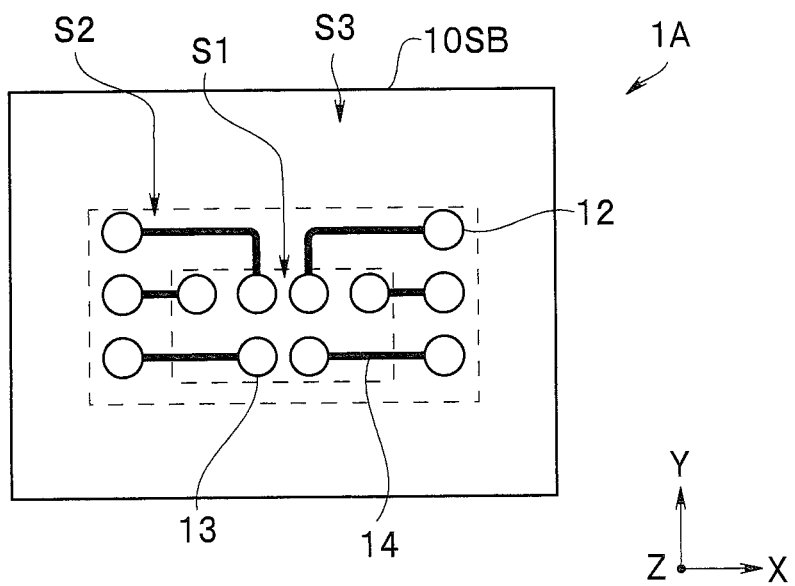
FIG. 4 is a rear view of an image pickup device of an image pickup module of a modification 1.

In contrast, in an image pickup module 1A, the bumps 15 which are the bonding portions between the first electrodes 13 and the second electrodes 23 are arranged in a grid as shown in FIG. 4. That is, the bumps 15 are not arranged in a circle. Arrangement of the bumps is not limited to a circular shape as long as the bumps are arranged only in the central area S1.

However, if stress applied to the image pickup module 1 via the signal cable 41 is isotropic in a plane orthogonal to the optical axis O, the image pickup module 1 in which the bumps 15 are arranged in a circle is more reliable than the image pickup module 1A.

<Modification 2 of First Embodiment>

Figure 5:
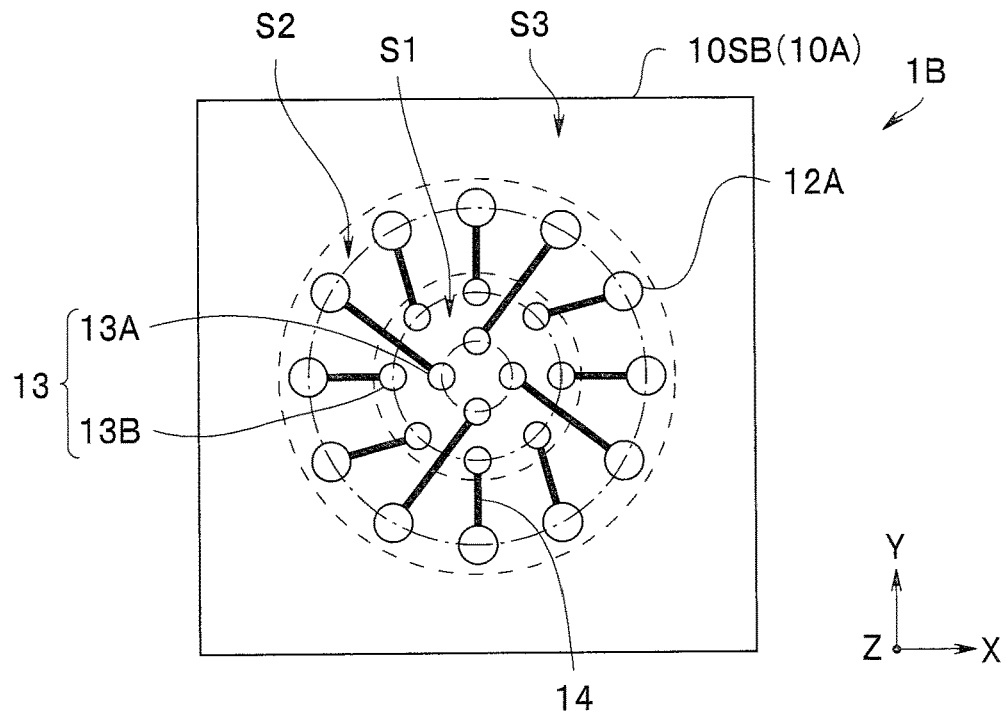
FIG. 5 is a rear view of an image pickup device of an image pickup module of a modification 2 of the first embodiment.

In an image pickup module 1B, the first electrodes 13 and the second electrodes 23 are concentrically arranged together as shown in FIG. 5. That is, the plurality of bumps 15 which are the bonding portions between the first electrodes 13 and the second electrodes 23 are arranged on circumferences of two circles having a same center point.

For example, the first electrodes 13 include first electrodes 13A arranged on a circumference of an inner circle and first electrodes 13B arranged on a circumference of an outer circle.

It is easy to arrange a lot of connection portions in the image pickup module 1B. Note that the bonding portions may be arranged on circumferences of three or more circles, and a bonding portion may be arranged on a center of the circles.

Note that an image pickup device 10A of the image pickup module 1B is of a back side illumination type, and through wires 12A connecting the light receiving portion and the second principal plane 10SB are arranged in a circle. In the image pickup device 10A of the back side illumination type, a part of the plurality of through wires 12A may be formed in an area facing the light receiving portion.

As already described, if stress applied to the image pickup module 1B via the signal cable 41 is isotropic in a plane orthogonal to the optical axis O, the image pickup module 1B in which the through wires 12A are arranged in a circle is more reliable than the image pickup module 1.

<Modification 3 of First Embodiment>

Figure 6:
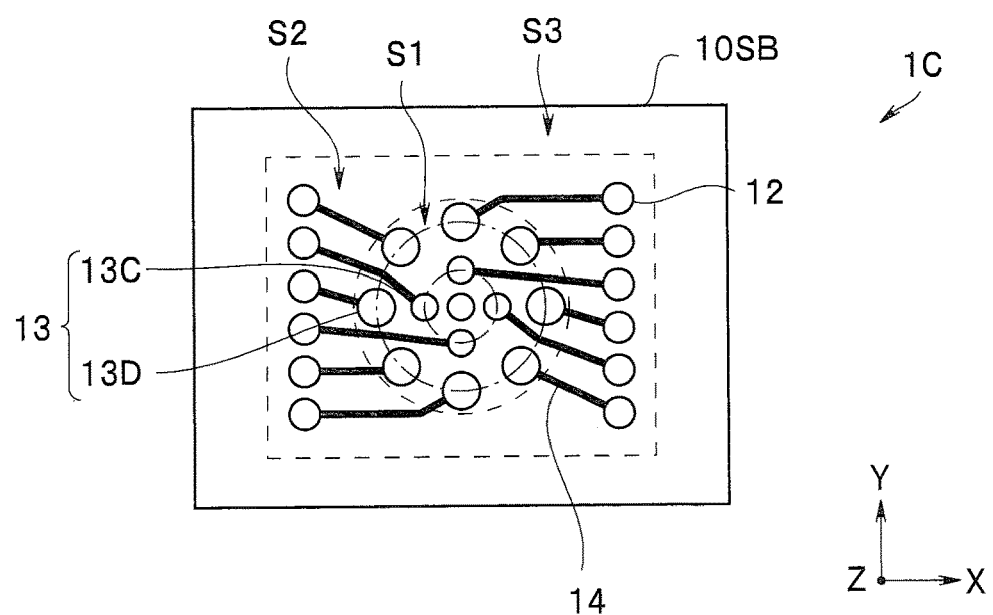
FIG. 6 is a rear view of an image pickup device of an image pickup module of a modification 3 of the first embodiment.

In an image pickup module 1C, the first electrodes 13 and the second electrodes 23, that is, the bumps 15 which are bonding portions are centrically arranged similarly to the image pickup module 1B as shown in FIG. 6.

An area (a size) of each of bonding portions arranged on an inner circumferential side in the direction orthogonal to the optical axis (that is, an XY plane direction) is smaller than an area (a size) of each of bonding portions arranged on an outer circumferential side among the bonding portions. The number of bonding portions on the inner circumferential side per unit area is larger than the outer circumferential side.

For example, the first electrodes 13 include first electrodes 13C arranged on a circumference of an inner circle and first electrodes 13D arranged on a circumference of an outer circle. A size of each of the first electrodes 13C is smaller than a size of each of the first electrodes 13D.

Since the bonding portions on the internal circumference are highly reliable because of being protected by the bonding portions with a large bonding area arranged on the outer circumference. Furthermore, since it is easy to arrange more bonding portions in an area near to the center (on the inner circumferential side), the image pickup module 1C is more reliable than the image pickup module 1B.

<Modification 4 of First Embodiment>

Figure 7:
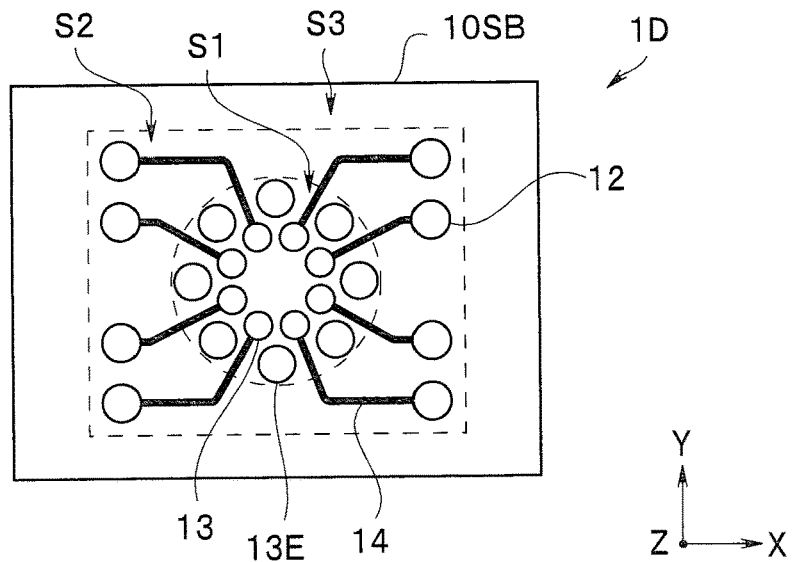
FIG. 7 is a rear view of an image pickup device of an image pickup module of a modification 4 of the first embodiment.

As shown in FIG. 7, an image pickup module 1D has dummy bonding portions that do not electrically connect the image pickup device 10 (the first semiconductor device) and the second semiconductor device 20, in the central area S1 on an outer circumferential side of the bonding portions.

For example, first dummy electrodes 13E that are not connected to the through wires 12 are disposed on the second principal plane 10SB of the image pickup device 10. The first dummy electrodes 13E are bonded to second dummy electrodes of the second semiconductor device 20 via the bumps 15 which are the bonding portions.

For example, the first dummy electrodes 13E are arranged in a manner of surrounding the first electrodes 13. That is, the first electrodes 13 are arranged only inside a polygon configured by connecting centers of the plurality of first dummy electrodes 13E.

Since the bonding portions are protected by the dummy bonding portions, the image pickup module 1D is more reliable.

Second Embodiment

Since an image pickup module 1E of a modification of a second embodiment is similar to the image pickup module 1 and the like and has the same effects, a component with a same function will be given a same reference numeral, and description of the component will be omitted.

Figure 8:
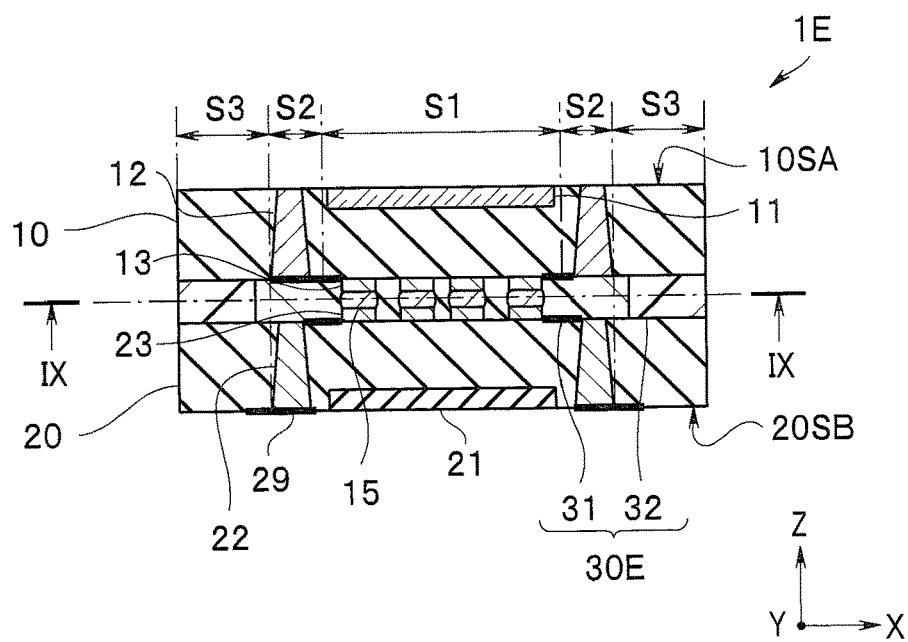
FIG. 8 is a cross-sectional view of an image pickup module of a second embodiment.
Figure 9:
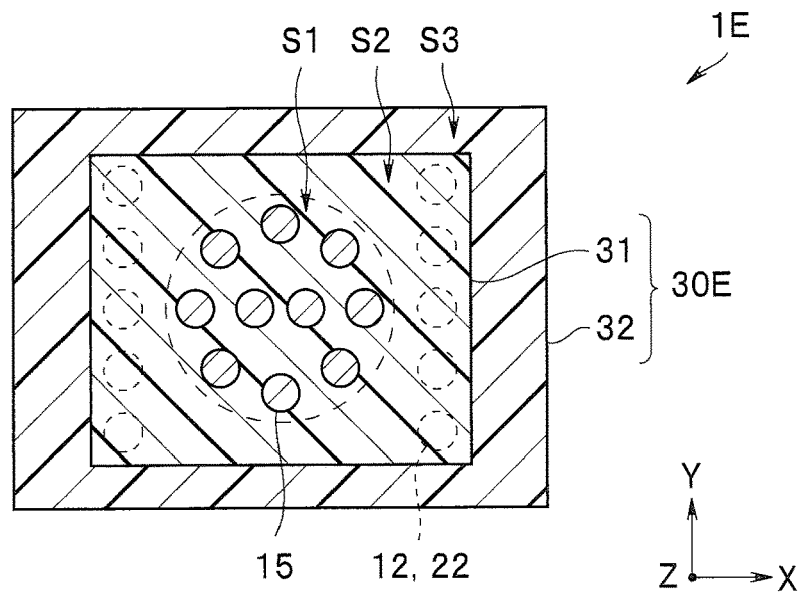
FIG. 9 is a cross-sectional view of the image pickup module of the second embodiment along a IX-IX line in FIG. 8.

In the image pickup module 1E of the present embodiment shown in FIGS. 8 and 9, a sealing layer 30E includes a first sealing layer 31 disposed in the central area S1 and the intermediate area S2 and a second sealing layer 32 with a Young's modulus smaller than a Young's modulus of the first sealing layer 31, which is disposed in the outer circumferential area S3.

For example, by disposing the first sealing layer 31 that has been patterned, on bonding surfaces before bonding the first semiconductor device (the image pickup device) 10 and the second semiconductor device 20, and injecting the second semiconductor device 20 into a gap between the bonding surfaces after bonding, the sealing layer 30E is disposed.

The central area S1 and the intermediate area S2 in which the bonding portions and the through wires are disposed are protected by the first sealing layer 31 with a high Young's modulus. For the outer circumferential area S3, the second sealing layer 32 that elastically deforms and absorbs stress is disposed.

Especially, it is preferable that the Young's modulus of the first sealing layer 31 is 1 GPa or more, and the Young's modulus of the second sealing layer 32 is between 1 MPa and 500 MPa, including 1 MPa and 500 MPa.

For example, the first sealing layer 31 is made of epoxy resin with a Young's modulus of 8 GPa, and the second sealing layer 32 is made of silicone resin with a Young's modulus of 50 MPa. Polymerization degrees of the first sealing layer 31 and the second sealing layer 32 made of same resin may be different from each other. Note that though the sealing layer 30E is configured with the first sealing layer 31 and the second sealing layer 32, the sealing layer 30E may further include a third sealing layer. For example, a Young's modulus of the third sealing layer disposed between the first sealing layer 31 and the second sealing layer 32 is smaller than the Young's modulus of the first sealing layer 31 and larger than the Young's modulus of the second sealing layer 32.

The image pickup module 1E is more reliable than the image pickup module 1 that has the single sealing layer 30.

Modification of Second Embodiment

In the image pickup module 1E, the intermediate area S2 in which the through wires 12 are disposed is also protected by the first sealing layer 31.

Figure 10:
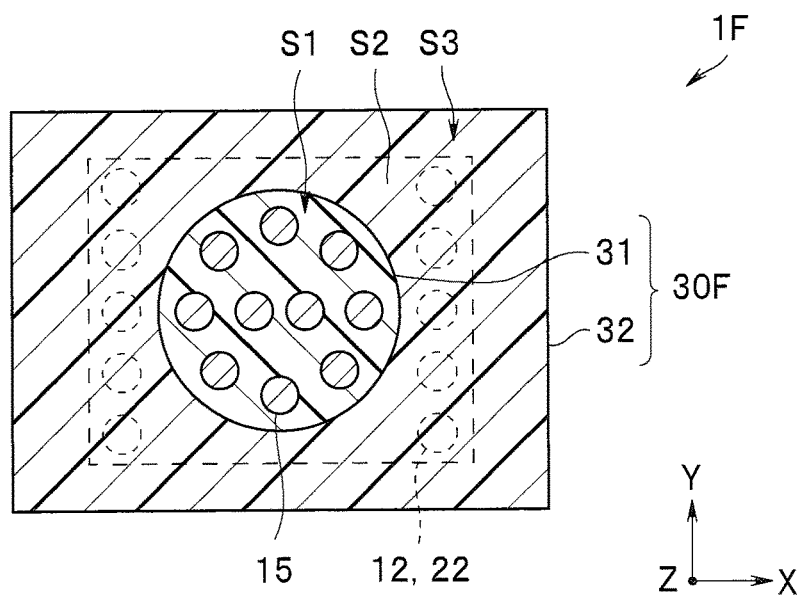
FIG. 10 is a cross-sectional view of an image pickup module of a modification of the second embodiment.

In contrast, in an image pickup module 1F of the present modification shown in FIG. 10, the second sealing layer 32 is disposed in the intermediate area S2 of a sealing layer 30F. Since the second sealing layer 32 with a large area has a strong stress absorption effect, the bonding portions disposed in the central area S1 can be protected more certainly.

Furthermore, since the first sealing layer 31 is in a circular shape, the first sealing layer 31 can be disposed by dropping liquid resin without performing patterning particularly.

It goes without saying that the image pickup modules 1E and 1F have the effects of the image pickup modules 1A to 1D by having bonding portions of the configuration of the image pickup modules 1A to 1D.

Third Embodiment

Since an image pickup module 1G of a modification of a third embodiment is similar to the image pickup module 1 and the like and has the same effects, a component with a same function will be given a same reference numeral, and description of the component will be omitted.

As shown in FIG. 11, in the image pickup module 1G, the image pickup device 10 (the first semiconductor device) and a plurality of semiconductor devices (second to fourth semiconductor devices) 20A to 20C are laminated via sealing layers 30E disposed among the plurality of semiconductor devices 10, and 20A to 20C, respectively. To a rear surface 20CSB of the fourth semiconductor device 20C, which is on a rearmost side of the image pickup module 1G, the signal cable 41 is connected via the circuit board 40 for which a flexible substrate is used and to which signal connection pad 49 is connected, via the external connection terminal 29.

Each of the plurality of semiconductor devices 10, and 20A to 20C is in almost the same configuration as the image pickup device 10 (the first semiconductor device) or the second semiconductor device 20 that has been already described, and the plurality of semiconductor devices 10, and 20A to 20C are laminated via the sealing layers 30E each of which is in almost the same configuration as the sealing layer 30.

For example, the third semiconductor device 20B has a fifth principal plane 20BSA and a sixth principal plane 20BSB facing the fifth principal plane 20BSA. The third semiconductor device 20B has a semiconductor circuit portion 21B in the central area S1 on the sixth principal plane 20BSB and has through wires 22B connected to the semiconductor circuit portion 21B in the intermediate area S2 surrounding the central area S1. The third semiconductor device 20B has the first electrodes 13B in the central area S1 on the fifth principal plane 20BSA and has second electrodes 23B connected to the first electrodes 13B via the through wires 22B, in the central area S1 on the sixth principal plane. Bonding portions between the third semiconductor device 20B and the second semiconductor device 20A and bonding portions between the third semiconductor device 20B and the fourth semiconductor device 20C are disposed only in the central area S1.

Note that a part of the plurality of first electrodes, the plurality of second electrodes and the through wires may be formed on an inner circumferential part of the semiconductor circuit portion or in an area facing the semiconductor circuit portion 21. On the contrary, the semiconductor circuit portion may be formed in the intermediate area or the outer circumferential area.

That is, the image pickup module of the embodiment may include three or more semiconductor devices if the image pickup device 10 is included. Especially, if the number of laminated semiconductor devices is four or more, the effects of the present invention are remarkable.

Note that in an image pickup module in which three or more semiconductor devices are laminated, it is only necessary that the same configuration as the image pickup module 1 or the like is adopted at least between any two devices. In an image pickup module in which four or more semiconductor devices are laminated, however, it is preferable that the configuration of the image pickup module 1 or the like is adopted between frontmost devices and between rearmost devices because strongest stress is applied.

Modification of Third Embodiment

Since an image pickup module 1H of a modification of the third embodiment is similar to the image pickup module 1G and has the same effects, a component with a same function will be given a same reference numeral, and description of the component will be omitted.

In the image pickup module 1G, since the circuit board 40 uses a flexible substrate having flexibility as a base, the cable 41 can be easily connected. In contrast, a circuit board 45 of the image pickup module 1H shown in FIG. 12 uses a rigid substrate is used as a base. The signal connection pad 49 of the circuit board 45 is bonded to the external connection terminal 29 of the semiconductor device 20C. Two signal cables 41 are connected to side surfaces of the circuit board 45, respectively.

That is, the circuit board may be flexible or inflexible. A plurality of signal cables 41 may be connected to a plurality of faces of the circuit board, respectively. Furthermore, the image pickup module may not use the circuit board but the signal cables 41 may be directly connected to the external connection terminal 29.

Fourth Embodiment

Since an image pickup module 1I of a fourth embodiment is similar to the image pickup module 1E and the like, a component with a same function will be given a same reference numeral, and description of the component will be omitted.

Figure 13:
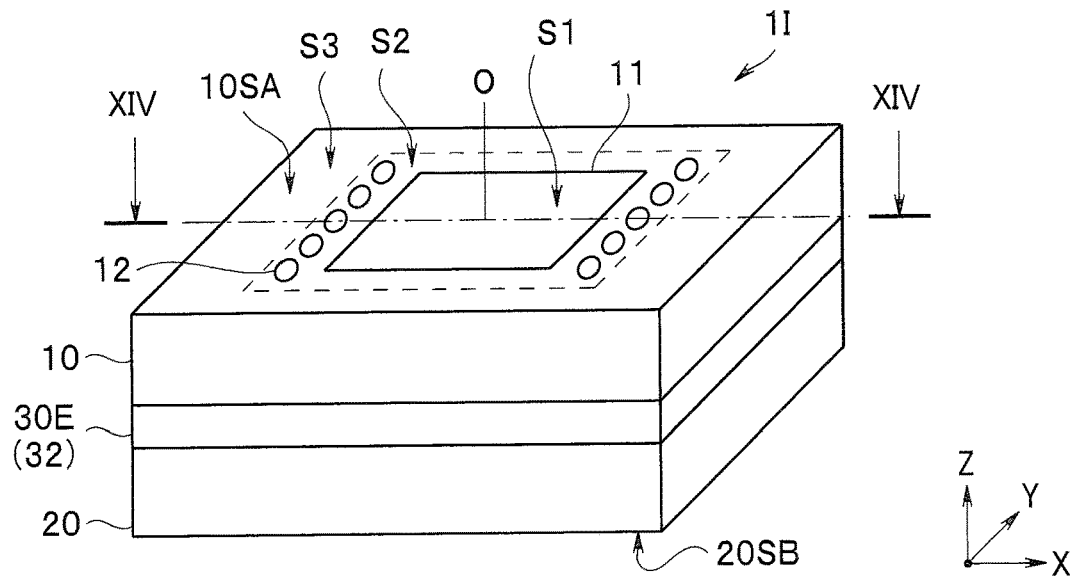
FIG. 13 is a perspective view of an image pickup module of a fourth embodiment.
Figure 14:
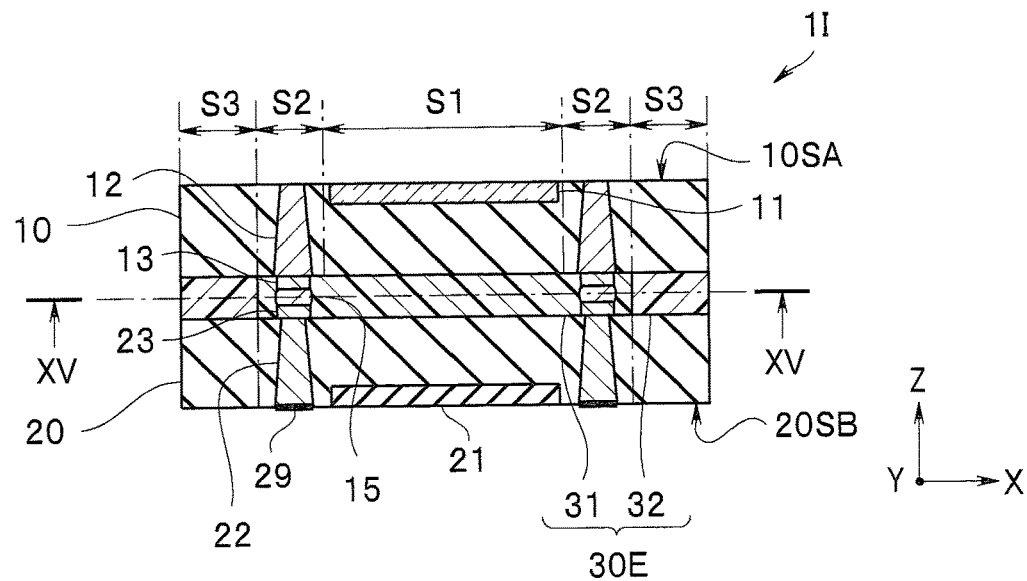
FIG. 14 is a cross-sectional view of the image pickup module of the fourth embodiment along a XIV-XIV line in FIG. 13.
Figure 15:
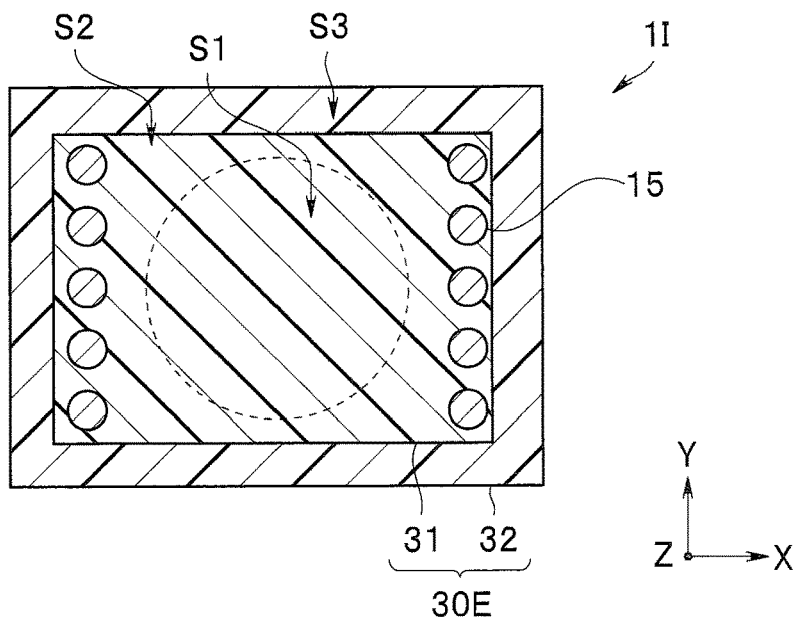
FIG. 15 is a cross-sectional view of an image pickup device of the image pickup module of the fourth embodiment along a XV-XV line in FIG. 14.

As shown in FIGS. 13, 14 and 15, in the image pickup module 1I, the first electrodes 13 and the second electrodes 23 are disposed in the intermediate area S2. That is, the bonding portions 15 are disposed in the intermediate area S2 where the through wires 12 and 22 are disposed.

The sealing layer 30E includes the first sealing layer 31 disposed in the central area S1 and the intermediate area S2 and the second sealing layer 32 with a Young's modulus smaller than a Young's modulus of the first sealing layer 31, which is disposed in the outer circumferential area S3 similarly to the image pickup module 1E.

The image pickup module 1I in which the second sealing layer 32 configured to elastically deform to absorb stress is disposed in the outer circumferential area S3 is highly reliable because stress applied to the bonding portions 15 and the through wires 12 and 22 is reduced similarly to the image pickup module 1E.

Modification of Fourth Embodiment

Since an image pickup module 1J of a modification of the fourth embodiment is similar to the image pickup module 1I, a component with a same function will be given a same reference numeral, and description of the component will be omitted.

Figure 16:
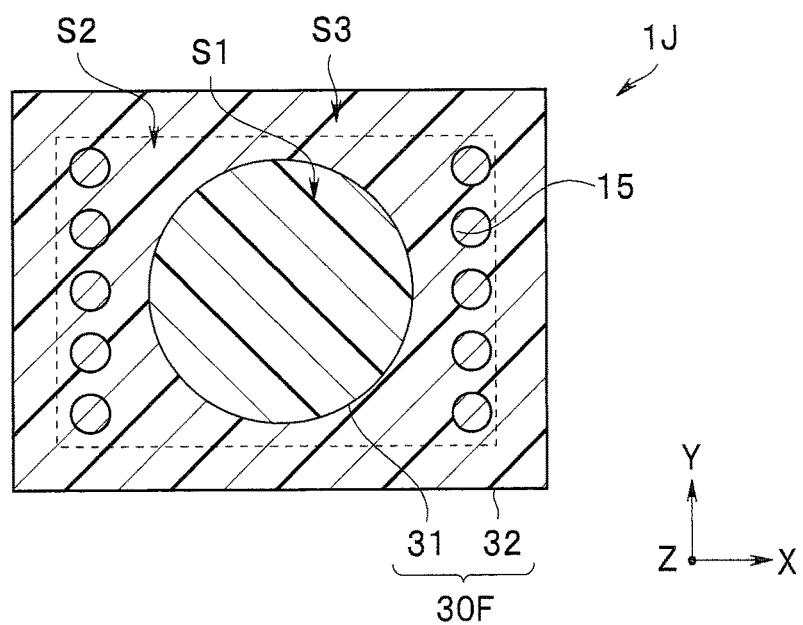
FIG. 16 is a rear view of an image pickup device of an image pickup module of a modification of the fourth embodiment.

As shown in FIG. 16, in the image pickup module 1J, the sealing layer 30F includes the first sealing layer 31 disposed in the central area S1 and the second sealing layer 32 with a Young's modulus smaller than a Young's modulus of the first sealing layer 31 disposed in the intermediate area S2 and the outer circumferential area S3.

The image pickup module 1J in which the second sealing layer 32 configured to elastically deform to absorb stress is disposed in the outer circumferential area S3 is highly reliable because stress applied to the bonding portions 15 and the through wires 12 and 22 is reduced similarly to the image pickup module 1I.

That is, in the intermediate area S2 of the image pickup module, the first sealing layer 31 or the second sealing layer 32 may be disposed.

Fifth Embodiment

Since an image pickup module 1K of a fifth embodiment is similar to the image pickup module 1C and the like and has the same effects, a component with a same function will be given a same reference numeral, and description of the component will be omitted.

Figure 17:
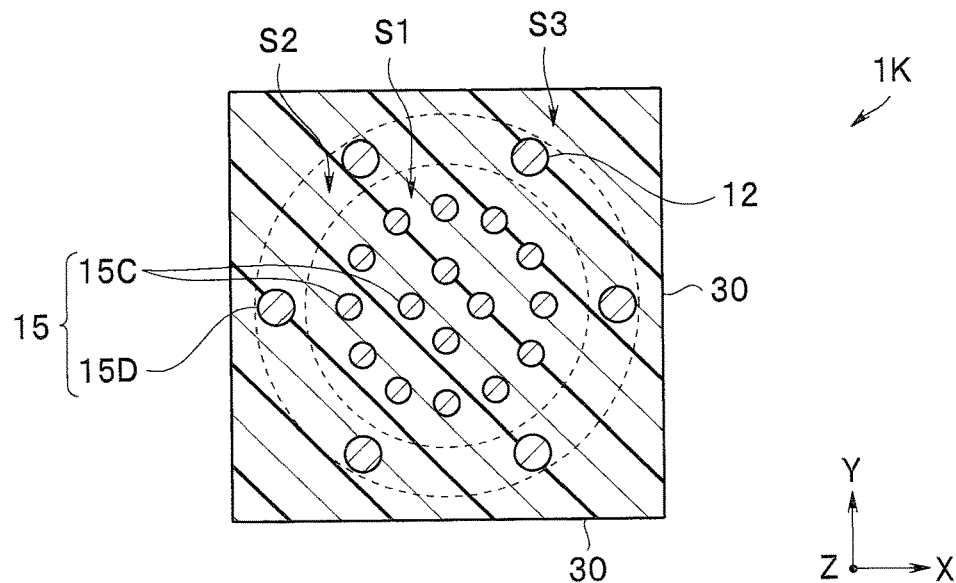
FIG. 17 is a cross-sectional view of an image pickup module of a fifth embodiment.

As shown in FIG. 17, in the image pickup module 1K, the plurality of bonding portions 15 are concentrically arranged, and a size of bonding portions 15C arranged on an inner circumferential side is smaller than a size of bonding portions 15D arranged on an outer circumferential side.

Note that, in the image pickup module 1K, the bonding portions 15D on an outermost circumference are directly bonded to through wires (not shown). In other words, the through wires exist above and below the bonding portions 15D (in a vertical direction on FIG. 17). On the other hand, through wires do not exist above or below the bonding portions 15C.

Among the bonding portions 15, the bonding portions 15D are disposed in the intermediate area S2. That is, the bonding portions 15 of the image pickup module 1K are disposed not only in the central area S1.

In the image pickup module 1K, the image pickup module and a second image pickup device are fixed by the large bonding portions 15D arranged on the outer circumferential side. Therefore, the small bonding portions 15C arranged on the inner circumferential side are also highly reliable, and it is easy to arrange more bonding portions 15 in an area near to a center (on the inner circumferential side).

Note that the plurality of bonding portions 15C may be annually arranged inside an area surrounded by line segments connecting the plurality of bonding portions 15D that are annually arranged. That is, a concentric shape in the present invention does not mean strict concentric circles but include a plurality of annular shapes having a same center.

Modification of Fifth Embodiment

Since an image pickup module 1L of a modification of the fifth embodiment is similar to the image pickup module 1K, a component with a same function will be given a same reference numeral, and description of the component will be omitted.

Figure 18:
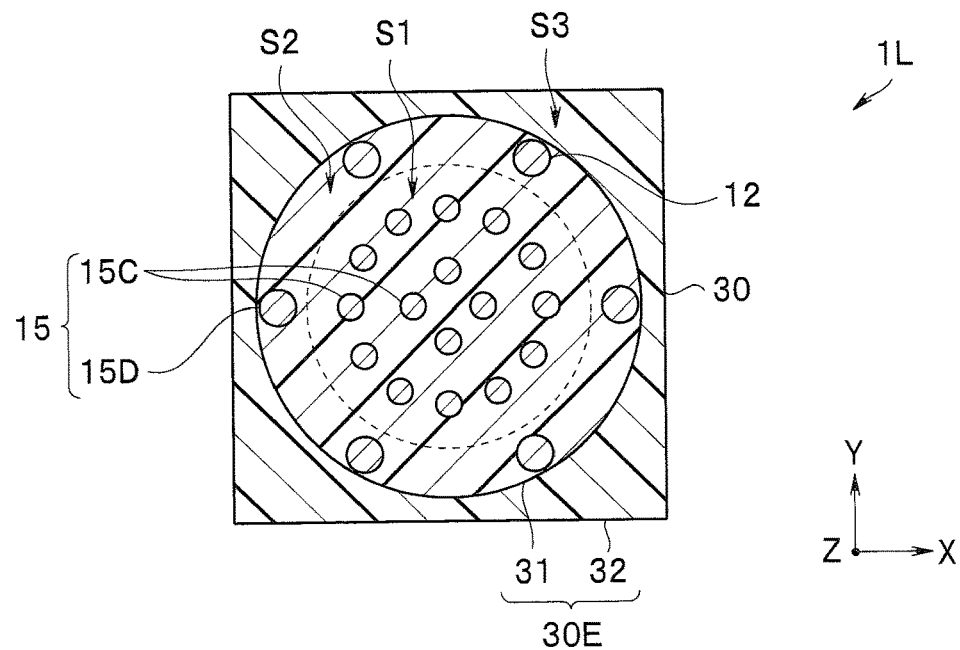
FIG. 18 is a cross-sectional view of an image pickup module of a modification of the fifth embodiment.

In the image pickup module 1K, the whole sealing layer 30 is made of same resin. In contrast, in the image pickup module 1L shown in FIG. 18, the sealing layer 30E includes the first sealing layer 31 disposed in the central area S1 and the intermediate area S2 and the second sealing layer 32 with a Young's modulus smaller than a Young's modulus of the first sealing layer 31, which is arranged in the outer circumferential area S3.

The image pickup module 1K is highly reliable because stress applied to the bonding portions 15C is reduced, similarly to the image pickup module 1I. Note that, as already described, the first sealing layer 31 may be disposed in the intermediate area S2.

Sixth Embodiment

Since an image pickup module 1M of a sixth embodiment is similar to the image pickup module 1I and the like and the like and has the same effects, a component with a same function will be given a same reference numeral, and description of the component will be omitted.

Figure 19:
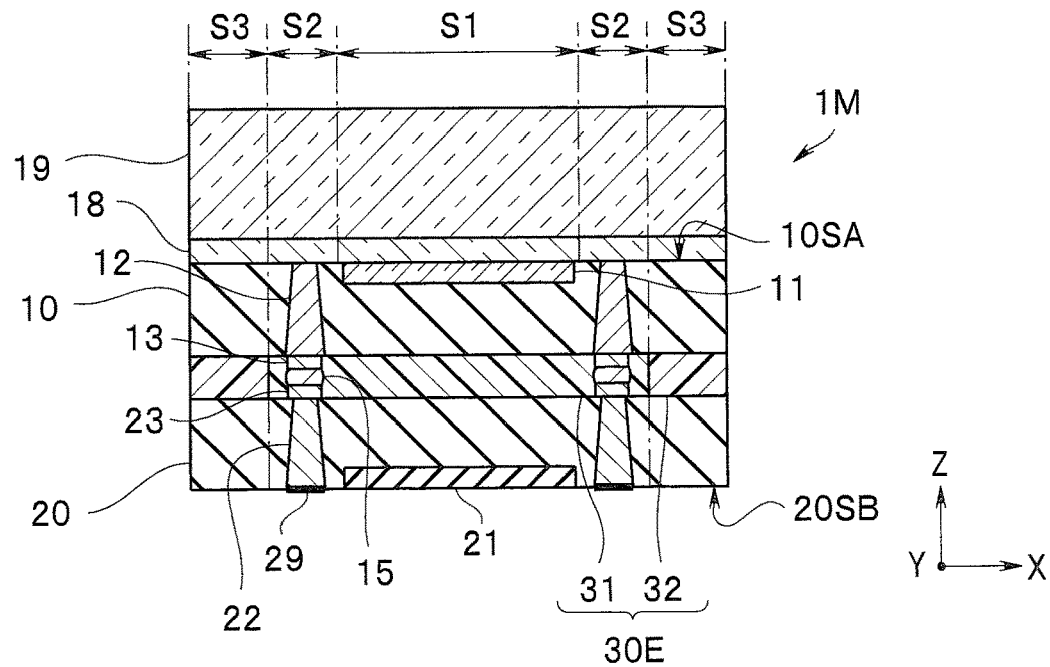
FIG. 19 is a cross-sectional view of an image pickup module of a sixth embodiment.

As shown in FIG. 19, the image pickup module 1M is further provided with cover glass 19 that is adhered to the first principal plane 10SA via an adhesive layer 18.

Figure 20:
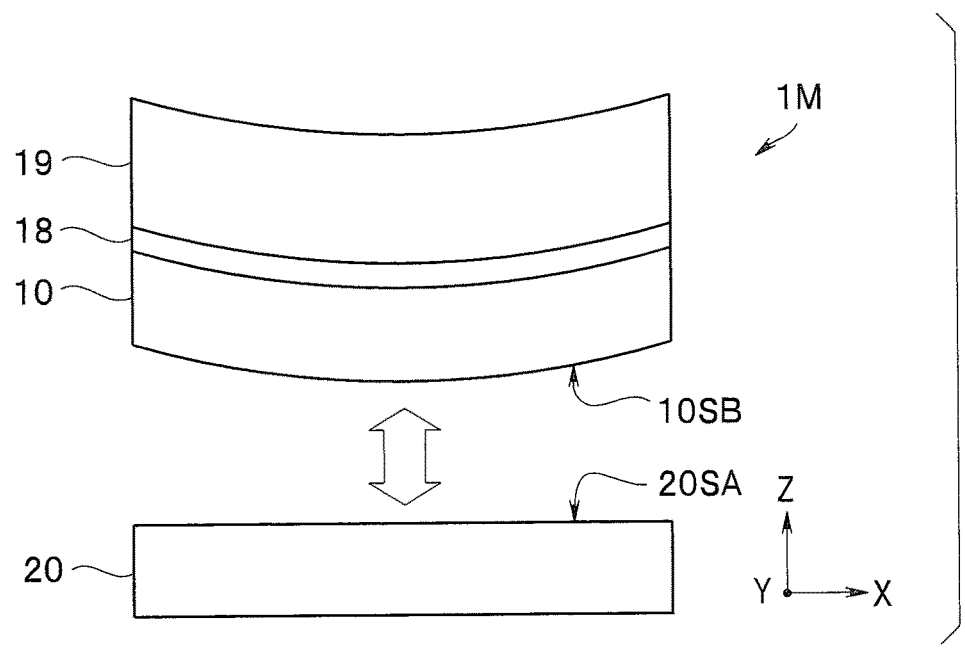
FIG. 20 is an exploded view for illustrating a method for manufacturing the image pickup module of the sixth embodiment.

As already described, when the cover glass 19 is adhered to the image pickup device 10 via the adhesive layer 18, the image pickup device 10 may bend and deform as shown in FIG. 20. When the second principal plane 10SB of the bent and deformed image pickup device 10 is bonded to the third principal plane 20SA of the second semiconductor device 20 in a flat plane shape via a sealing layer, the deformation is corrected. Then, the outer circumferential area S3 of the adhesive layer 18 may detached, and reliability may decrease. Note that though the deformation is emphasized in FIG. 20, an actual amount of deformation is, for example, only 1 μm at an end portion of the outer circumferential area S3 in an image pickup module with outer dimensions of 3 mm×3 mm.

In the image pickup module 1M, the sealing layer 30E includes the first sealing layer 31 disposed in the central area S1 and the intermediate area S2 and the second sealing layer 32 with a Young's modulus smaller than a Young's modulus of the first sealing layer 31, which is disposed in the outer circumferential area S3.

In the image pickup module 1M, since the second sealing layer 32 disposed in the outer circumferential area S3 easily deforms, the image pickup device 10 and the cover glass 19 are adhered to the image pickup device 10 in a state of being bent and deformed. Therefore, since the outer circumferential area S3 may not be detached, the image pickup module 1L is highly reliable.

Note that if the resin of the sealing layer 30 is curable resin, the outer circumferential area S3 may be detached due to shrinkage stress at the time of curing. Therefore, it is preferable that a curing shrinkage rate of the second sealing layer 32 is low, and it is especially preferable that the curing shrinkage rate is 3% or less. If the curing shrinkage rate is 3% or less, shrinkage stress acting on the outer circumferential area S3 is small, and the outer circumferential area S3 may not be detached. Therefore, reliability is high.

Figure 12:
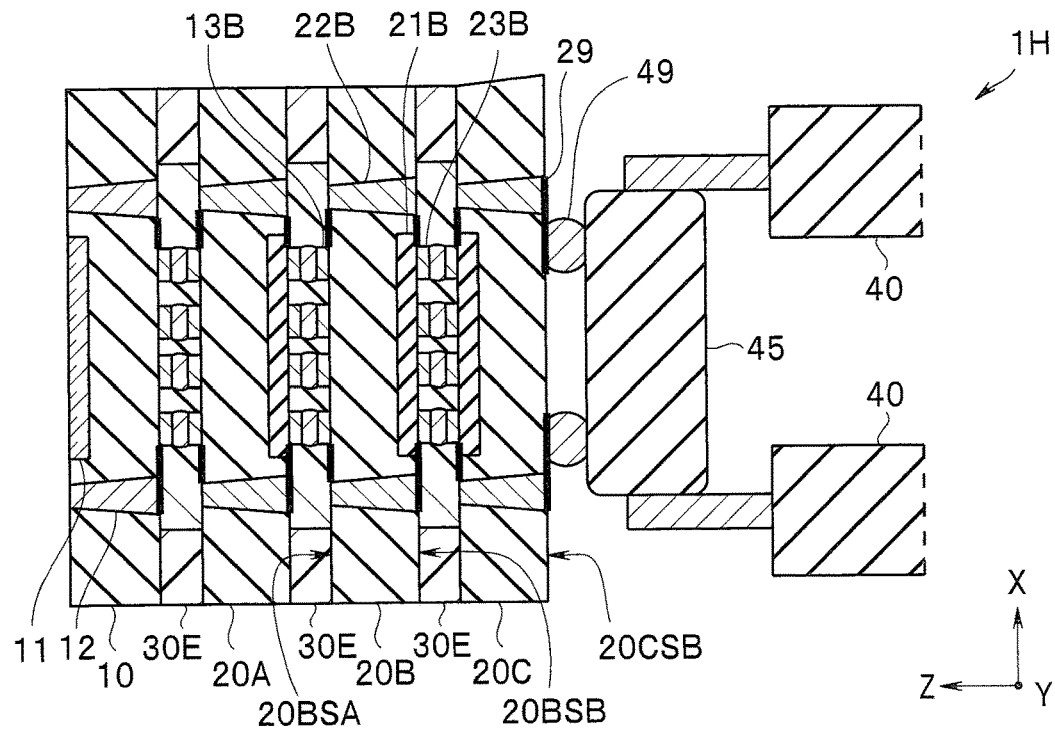
FIG. 12 is a cross-sectional view of an image pickup module of a modification of the third embodiment.

Note that, in the image pickup modules 1I to 1M, the configuration of the external connection terminal on the rear surface and the like are also the same as the image pickup modules 1G and 1H shown in FIGS. 11 and 12, and three or more semiconductor devices may be included.

Seventh Embodiment

An endoscope of a seventh embodiment is provided with any of the image pickup modules 1, and 1A to 1M.

Figure 21:
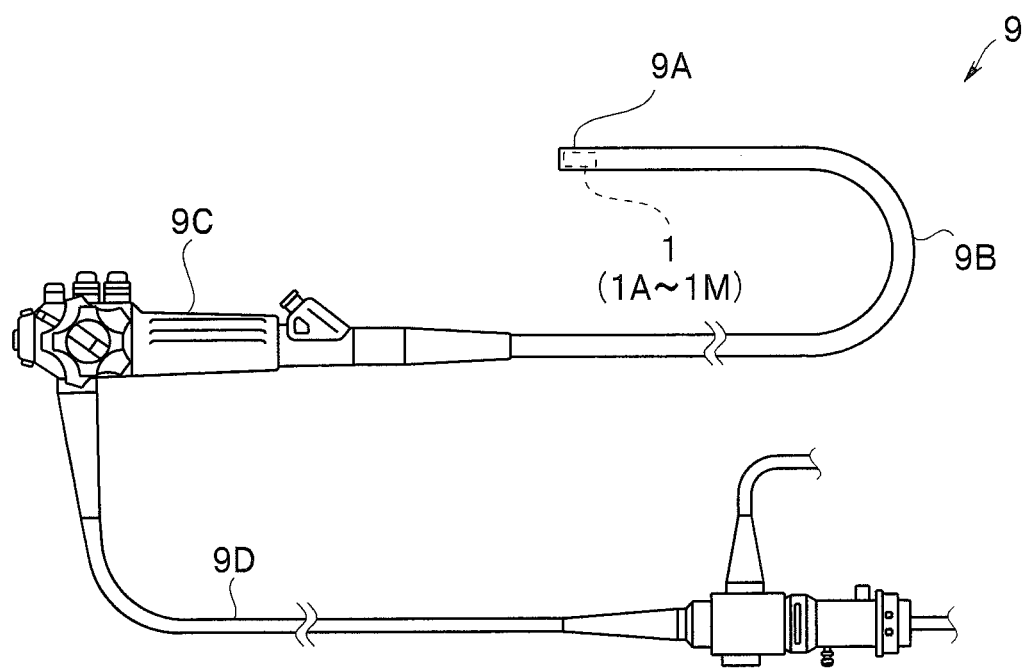
FIG. 21 is a perspective view of an endoscope of a seventh embodiment.

As shown in FIG. 21, for example, an endoscope 9 is provided with an insertion portion 9B in which the image pickup module 1 is accommodated in the distal end portion 9A, an operation portion 9C disposed on a proximal end side of the insertion portion 9B, and a universal cord 9D extending from the operation portion 9C. The universal cord 9D is connected to the signal cable 41 of the image pickup module 1.

Since the endoscope 9 has any of the image pickup modules 1, and 1A to 1M in the distal end portion 9A of the insertion portion 9B, the endoscope 9 is highly reliable. Note that though the endoscope 9 is a flexible endoscope, the endoscope 9 may be a rigid endoscope. The endoscope 9 may be a medical endoscope or an industrial endoscope.

Though the image pickup module 1 and the like have been described, the image pickup module of the present invention is not limited to use for an endoscope. More specifically, such an image pickup apparatus that stress is applied to an image pickup module by a signal cable connected to the image pickup module moving, the same effects can be obtained by adopting the same configuration of an image pickup module of the present invention. The image pickup module of the present invention is applicable to apparatuses other than an endoscope, for example, like an image pickup module mounted on a distal end portion of a movable ultra miniature robot arm and an image pickup module that performs focus adjustment and the like by moving not a lens unit but the image pickup module in an optical axis direction.

The present invention is not limited to the embodiments and modifications described above, but various changes, alterations, combinations and the like are possible within a range not changing the spirit of the present invention.

What is claimed is:

1. An image pickup module comprising:
   a plurality of semiconductor devices including image pickup devices; and
   sealing layers disposed between the plurality of semiconductor devices respectively;
   the image pickup module transmitting a signal via a signal cable connected to a rear surface; wherein
   a first semiconductor device among the plurality of semiconductor devices includes a first principal plane and a second principal plane facing the first principal plane and includes a semiconductor circuit portion in a central area on the first principal plane, first through wires connected to the semiconductor circuit portion existing in an intermediate area surrounding the central area, and first electrodes connected to the first through wires being disposed on the second principal plane;
   a second semiconductor device among the plurality of semiconductor devices includes a third principal plane and a fourth principal plane facing the third principal plane, second electrodes bonded to the first electrodes via bonding portions being disposed on the third principal plane, and second through wires connected to the second electrodes existing in the intermediate area;
   an external connection terminal is disposed on the rear surface of a semiconductor device on a rearmost side among the plurality of semiconductor devices, the signal cable being connected to the external connection terminal, and the external connection terminal being connected to the second through wires; and
   the sealing layers include a first sealing layer disposed in the central area and a second sealing layer disposed in an outer circumferential area surrounding the intermediate area and with a Young's modulus smaller than a Young's modulus of the first sealing layer.

2. The image pickup module according to claim 1, wherein the first sealing layer is disposed in the intermediate area.

3. The image pickup module according to claim 1, wherein the second sealing layer is disposed in the intermediate area.

4. The image pickup module according to claim 1, further comprising cover glass adhered to the first principal plane via an adhesive layer.

5. The image pickup module according to claim 4, wherein a curing shrinkage rate of the second sealing layer is 3% or less.

6. The image pickup module according to claim 1, wherein the bonding portions between the first electrodes and the second electrodes are disposed only in the central area.

7. The image pickup module according to claim 1, wherein the first semiconductor device is the image pickup device the semiconductor circuit portion of which is a light receiving portion.

8. The image pickup module according to claim 1, wherein each of the plurality of semiconductor devices is in a configuration similar to a configuration of the first semiconductor device or the second semiconductor device, and the plurality of semiconductor devices are laminated via a sealing layer with a same configuration as the sealing layer.

9. An image pickup module comprising:
   a plurality of semiconductor devices including image pickup devices; and
   sealing layers disposed between the plurality of semiconductor devices respectively;
   the image pickup module transmitting a signal via a signal cable connected to a rear surface; wherein
   a first semiconductor device among the plurality of semiconductor devices includes a first principal plane and a second principal plane facing the first principal plane and includes a semiconductor circuit portion on the first principal plane, first electrodes connected to through wires being disposed on the second principal plane;
   a second semiconductor device among the plurality of semiconductor devices includes a third principal plane and a fourth principal plane facing the third principal plane, second electrodes bonded to the first electrodes via bonding portions being disposed on the third principal plane;
   an external connection terminal is disposed on the rear surface of a semiconductor device on a rearmost side among the plurality of semiconductor devices, the signal cable being connected to the external connection terminal, and the external connection terminal being connected to the second electrodes; and
   the plurality of semiconductor devices are bonded via a plurality of bonding portions, the plurality of bonding portions being concentrically arranged; and a size of the bonding portions arranged on an inner circumferential side is smaller than a size of the bonding portions arranged on an outer circumferential side.

10. The image pickup module according to claim 9, wherein the sealing layers include a first sealing layer disposed in a central area where the semiconductor circuit portion is formed and a second sealing layer disposed in an outer circumferential area surrounding an intermediate area where the through wires are disposed and with a Young's modulus smaller than a Young's modulus of the first sealing layer.

11. The image pickup module according to claim 9, wherein the bonding portions between the first electrodes and the second electrodes are disposed only in the central area where the semiconductor circuit portion is formed.

12. An endoscope comprising:

an image pickup module comprising: a plurality of semiconductor devices including image pickup devices, and sealing layers disposed between the plurality of semiconductor devices respectively, the image pickup module transmitting a signal via a signal cable connected to a rear surface, a first semiconductor device among the plurality of semiconductor devices including a first principal plane and a second principal plane facing the first principal plane and including a semiconductor circuit portion in a central area on the first principal plane, first through wires connected to the semiconductor circuit portion existing in an intermediate area surrounding the central area, and first electrodes connected to the first through wires being disposed on the second principal plane; a second semiconductor devices among the plurality of semiconductor devices including a third principal plane and a fourth principal plane facing the third principal plane, second electrodes bonded to the first electrodes via bonding portions being disposed on the third principal plane, and second through wires connected to the second electrodes existing in the intermediate area; an external connection terminal being disposed on the rear surface of a semiconductor device on a rearmost side among the plurality of semiconductor devices, the signal cable being connected to the external connection terminal, and the external connection terminal being connected to the second through wires; and the sealing layers including a first sealing layer disposed in the central area and a second sealing layer disposed in an outer circumferential area surrounding the intermediate area and with a Young's modulus smaller than a Young's modulus of the first sealing layer;

the signal cable connected to the external connection terminal;

an insertion portion where the image pickup module is accommodated in a distal end portion;

an operation portion disposed on a proximal end side of the insertion portion; and a universal cord extending from the operation portion, the universal cord being electrically connected to the signal cable.

* * * * *